(12) United States Patent
Muzio et al.

(10) Patent No.: US 6,380,162 B1
(45) Date of Patent: Apr. 30, 2002

(54) ICE INHIBITING PEPTIDES

(75) Inventors: Marta Muzio, Milan; Martino Introna, Rho; Alberto Mantovani, Milan, all of (IT)

(73) Assignee: Applied Research Systems ARS Holding N.V., Curacao (AN)

( * ) Notice: Subject to any disclaimer, the term of this patent is extended or adjusted under 35 U.S.C. 154(b) by 0 days.

(21) Appl. No.: 09/297,369

(22) PCT Filed: Oct. 31, 1996

(86) PCT No.: PCT/EP96/04738

§ 371 Date: Jul. 1, 1999

§ 102(e) Date: Jul. 1, 1999

(87) PCT Pub. No.: WO98/18823

PCT Pub. Date: May 7, 1998

(51) Int. Cl.$^7$ .................. A61K 38/10; A61K 38/16; C07K 7/00

(52) U.S. Cl. .................. 514/13; 514/2; 514/12; 530/324; 530/325; 530/326

(58) Field of Search .................. 514/2, 12, 13; 530/324–326

(56) References Cited

U.S. PATENT DOCUMENTS 5,981,713 A * 11/1999 Colotta et al. ............ 530/397.9

FOREIGN PATENT DOCUMENTS

WO          96/12022          4/1996

OTHER PUBLICATIONS

Muzio et al., "Cloning and characterization of a new isoform of the interleukin 1 receptor antagonist", *J. Exp. Med*, 182:623–628 (Aug. 1995).
XP 000574812 "Identification and inhibition of the ICE/CED–3 protease necessary for mammalian apoptosis", *Nature*, 376:37–43 (Jul. 1995).
Thornberry et al., "A novel heterodimeric cysteine protease is required for interleukin–1β processing in monocytes", *Nature*, 356:768–774 (Apr. 1992).
Kamens et al., "Identification and characterization of ICH–2, a novel member of the interleukin–1β converting enzyme family of cysteine proteases", *The Journal of Biological Chemistry*, 270:15250–15257 (Jun. 1995).
Cerretti et al., "Molecular cloning of the interleukin–1β converting enzyme", *Science*, 256:97–100 (Apr. 1992).
Kumar et al., "Induction of apoptosis by the mouse Nedd2 gene, which encodes a protein similar to the product of the *Caenorhabditis elegans* cell death gene ced–3 and the mammalian IL–1β–converting enzyme", *Genes & Development*, 8:1613–1626 (1994).

Fernandes–Alnemri et al., "CPP32, a novel human apoptotic protein with homology to *Caenorhabditis elegans* cell death protein Ced–3 and mammalian interleukin–1β–converting enzyme", *The Journal of Biological Chemistry*, 269:30760–30765 (1994).
Munday et al., "Molecular cloning and pro–apoptotic activity of ICE$_{rel}$II and ICE$_{rel}$III, members of the ICE/CED–3 family of cysteine proteases", *The Journal of Biological Chemistry*, 270:15870–15877 (1995).
Faucheu et al., "A novel human protease similar to the interleukin–1β converting enzyme induces apoptosis in transfected cells", *Oxford University Press*, 1914–1923 (1995).
Griffin et al., "Structural analysis of proteins by capillary HPLC electrospray tandem mass spectrometry", *International Journal of Mass Spectrometry and Ion Processes*, 111:131–149 (1991).
Cameron et al., "Amino acid sequence analysis of human interleukin 1 (IL–1)", *J. Exp. Med.*, 162:790–801 (Sep. 1985).
Mosley et al., "The interleukin–1 receptor binds the human interleukin–1α precursor but not the interleukin–1β precursor", *The Journal of Biological Chemistry*, 262:2941–2944 (1987).
Kostura et al. "Identification of a monocyte specific pre–interleukin 1β convertase activity", *Proc. Natl. Acad. Sci. USA*, 86:5227–5231 (Jul. 1989).
Black et al. "Activation of interleukin–1β by a co–induced protease", *FEBS Letters*, 247:386–390 (Apr. 1989).
Howard et al., "IL–1–converting enzyme requires aspartic acid residues for processing of the IL–1β precursor at two distinct sites and does not cleave 31–kDa IL–1α", *The Journal of Immunology*, 147:2964–2969 (Nov. 1991).
Miura et al., "Induction of apoptosis in fibroblasts by IL–1β–converting enzyme, a mammalian homolog of the *C. elegans* cell death gene ced–3", *Cell*, 75:653–660 (1993).
Dinarello, "Interleukin–1 and interleukin–1 antagonism", *Blood*, 77:1627–1652 (Apr. 1991).
Colotta et al., "Interleukin–1 typeII receptor: A decoy target for IL–1 that is regulated by IL–4", *Science*, 261:472–475 (Jul. 1993).

(List continued on next page.)

*Primary Examiner*—Bennett Celsa
(74) *Attorney, Agent, or Firm*—Browdy and Neimark, P.L.L.C.

(57) ABSTRACT

The present invention relates to a peptide capable of binding to ICE and/or to enzymes of the ICE family, which peptide consists essentially of the amino acid sequence of SEQ ID NO:1 reported in the Sequence Listing, in which Xaa is selected between Asp and Ala, optionally containing one or more amino acids at its N-terminal and/or C-terminal end. It also relates to the use of the above peptide, for the preparation of pharmaceutical compositions active in pathologies requiring ICE inhibition and/or inhibition of enzymes of the ICE family.

20 Claims, 6 Drawing Sheets

OTHER PUBLICATIONS

Sims et al., "Interleukin 1 signaling occurs exclusively via the type I receptor", *Proc. Natl. Acad. Sci. USA,* 90:6155–6159 (1993).

Colotta et al., "The type II 'decoy' receptor: a novel regulatory pathway for interleukin 1", *Immunology Today,* 15:562–565 (1994).

Hannum et al., "Interleukin–1 receptor antagonist activity of a human interleukin–1 inhibitor", *Nature,* 343:336–343 (Jan. 1990).

Eisenberg et al., "Primary structure and functional expression from complementary DNA of a human interleukin–1 receptor antagonist", *Nature,* 343:341–343 (Jan. 1990).

Carter et al., "Purification, cloning, expression and biological characterization of an interleukin–1 receptor antagonist protein", *Nature,* 344:633–638 (Apr. 1990).

Yuan et al., The *C. elegans* cell death gene ced–3 encodes a protein similar to mammalian interleukin–1β–converting enzyme, *Cell,* 75:641–652 (1993).

Wang et al., "Ich–1, an Ice/ced–3–related gene, encodes both positive and negative regulators of programmed cell death", *Cell,* 78:739–750 (1994).

Nicholson et al., "Identification and inhibition of the ICE/CED–3 protease necessary for mammalian apoptosis", *Nature,* 376:37–43 (Jul. 1995).

Tewari et al., "Yama/CPP32β, a mammalian homolog of CED–3, is a CrmA–inhibitable protease that cleaves the death substrate poly(ADP–ribose) polymerase", *Cell,* 81:801–809 (Jun. 1995).

Fernandes–Alnemri et al., "Mch2, a new member of the apoptotic Ced–3/Ice cysteine protease gene family", *Cancer Research,* 55:2737–2742 (Jul. 1995).

Duan et al., "ICE–LAP–3, a novel mammalian homologue of the *Caenorhabditis elegans* cell death protein Ced–3 is activated during Fas– and tumor necrosis factor–induced apoptosis", *The Journal of Biological Chemistry,* 1621–1625 (1996).

Fernandes–Alnemri et al., "Mch3, a novel human apoptotic cysteine protease highly related to CPP32[1]", *Cancer Research,* 55:6045–6052 (Dec. 1995).

Lippke et al., "Identification and characterization of CPP32/Mch2 homolog 1, a novel cysteine protease similarly to CPP32", *The Journal of Biological Chemistry,* 271:1825–1828 (1996).

Duan et al., "ICE–LAP6, a novel member of the ICE/Ced–3 gene family, is activated by the cytotoxic T cell protease granzyme B" *The Journal of Biological Chemistry,* 271:16720–16724 (1996).

Muzio et al., "FLICE, a novel FADD–homologous ICE/CED–3–like protease, is recruited to the CD95 (Fas/APO–1) death–inducing signaling complex", *Cell,* 85:817–827 (1996).

Boldin et al., "Involvement of MACH, a novel MORTI/FADD–interacting protease, in Fas/APO–1– and TNF receptor–induced cell death", *Cell,* 85:803–815 (1996).

* cited by examiner

Peptide Sequences

A)
Glu-Gly-Glu-Asp-Asn-Ala-Asp-Ser-Lys

C)
Met-Ala-Leu-Ala-Asp-Leu-Tyr-Glu-Glu-Gly-Gly-Gly-Gly-Gly-Gly-Glu-Gly-Glu-Asp-Asn-Ala-Asp-Ser-Lys

S)
Met-Ala-Leu-Ala-Ala-Leu-Tyr-Glu-Glu-Gly-Gly-Gly-Gly-Gly-Gly-Glu-Gly-Glu-Asp-Asn-Ala-Ala-Ser-Lys

X)
Phe Lys Asp Pro His Gly Leu Trp Lys Gly Leu Ser His

B)
Ac-Tyr-Val-Ala-Asp-CHO

SEQUENCE LISTING

```
<160> NUMBER OF SEQ ID NOS: 10

<210> SEQ ID NO 1
<211> LENGTH: 19
<212> TYPE: PRT
<213> ORGANISM: Artificial Sequence
<220> FEATURE:
<223> OTHER INFORMATION: Xaa at positions 2 and 19 is an amino acid
      preferably selected between Asp and Ala; more
      preferably, it is Asp.
<223> OTHER INFORMATION: Description of Artificial Sequence:synthetic

<400> SEQUENCE: 1

Ala Xaa Leu Tyr Glu Glu Gly Gly Gly Gly Gly Glu Gly Glu Asp
 1               5                  10                  15

Asn Ala Xaa

<210> SEQ ID NO 2
<211> LENGTH: 19
<212> TYPE: PRT
<213> ORGANISM: Artificial Sequence
<220> FEATURE:
<223> OTHER INFORMATION: Description of Artificial Sequence:synthetic

<400> SEQUENCE: 2

Ala Asp Leu Tyr Glu Glu Gly Gly Gly Gly Gly Glu Gly Glu Asp
 1               5                  10                  15

Asn Ala Asp

<210> SEQ ID NO 3
<211> LENGTH: 19
<212> TYPE: PRT
<213> ORGANISM: Artificial Sequence
<220> FEATURE:
```

<223> OTHER INFORMATION: Description of Artificial Sequence:synthetic

<400> SEQUENCE: 3

Ala Ala Leu Tyr Glu Glu Gly Gly Gly Gly Gly Glu Gly Glu Asp
 1               5                  10                  15

Asn Ala Ala

<210> SEQ ID NO 4
<211> LENGTH: 24
<212> TYPE: PRT
<213> ORGANISM: Artificial Sequence
<220> FEATURE:
<223> OTHER INFORMATION: Description of Artificial Sequence:synthetic

<400> SEQUENCE: 4

Met Ala Leu Ala Asp Leu Tyr Glu Glu Gly Gly Gly Gly Gly Glu
 1               5                  10                  15

Gly Glu Asp Asn Ala Asp Ser Lys
            20

<210> SEQ ID NO 5
<211> LENGTH: 24
<212> TYPE: PRT
<213> ORGANISM: Artificial Sequence
<220> FEATURE:
<223> OTHER INFORMATION: Description of Artificial Sequence:synthetic

<400> SEQUENCE: 5

Met Ala Leu Ala Ala Leu Tyr Glu Glu Gly Gly Gly Gly Gly Glu
 1               5                  10                  15

Gly Glu Asp Asn Ala Ala Ser Lys
            20

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence:synthetic

<400> SEQUENCE: 6

Glu Gly Glu Asp Asn Ala Asp Ser Lys
1                   5

<210> SEQ ID NO 7
<211> LENGTH: 13
<212> TYPE: PRT
<213> ORGANISM: Artificial Sequence
<220> FEATURE:
<223> OTHER INFORMATION: Description of Artificial Sequence:synthetic

<400> SEQUENCE: 7

Phe Lys Asp Pro His Gly Leu Trp Lys Gly Leu Ser His
 1               5                  10

<210> SEQ ID NO 8
<211> LENGTH: 4
<212> TYPE: PRT
<213> ORGANISM: Artificial Sequence
<220> FEATURE:
<223> OTHER INFORMATION: Tyr at position 1 is acetylated; Asp at
      position 4 is modified with -CHO.
<223> OTHER INFORMATION: Description of Artificial Sequence:synthetic

<400> SEQUENCE: 8

```
Tyr Val Ala Asp
  1

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence:synthetic

<400> SEQUENCE: 9
aaaagccatg gccgacaagg tc                                          22

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence:synthetic

<400> SEQUENCE: 10
tctcttcacc ctgcccacag ac                                          22
```

ICE INHIBITING PEPTIDES

CROSS REFERENCE TO RELATED APPLICATION

The present application is the national stage under 35 U.S.C. 371 of PCT/EP96/04738, filed Oct. 31, 1996.

FIELD OF THE INVENTION

The present invention relates to a peptide capable of binding to ICE and/or to enzymes of the ICE family, which peptide consists essentially of the amino acid sequence of SEQ ID NO:1, in which Xaa is selected between Asp and Ala, optionally containing one or more amino acids at its N-terminal and/or C-terminal end.

It also relates to the use of the above peptide, for the preparation of pharmaceutical compositions active in pathologies requiring ICE inhibition and/or inhibition of enzymes of the ICE family.

BACKGROUND OF THE INVENTION

ICE (Interleukin-1β-Converting Enzyme) is a heterodimeric cysteine protease that has been recently purified and cloned (1). Interleukin-1β (IL-1β) is synthesised as an inactive 33 kDa or 31 kDa precursor (pIL-1β); the fully active 17.5 kDa mature form of IL-1β begins at Ala$^{117}$ and seems to result from processing between Asp$^{116}$ and Ala$^{117}$ (2,3). IL-1β precursor protein is, therefore, cleaved by ICE in the mature and biologically active form.

ICE activity has been identified in monocytes and THP1 cells, which cleave pIL-1β at Asp$^{116}$-Ala$^{117}$ as well Asp$^{27}$-Gly$^{28}$ to yield products of 17.5 kDa and 28 kDa, respectively (3,4). Cleavage at each site is dependent on aspartic acid in the P1position (4,6,7).

It is becoming apparent that cysteine proteases related to the *Caenorhabditis elegans* cell death protein ced-3 represent the effector components of the apoptotic machinery. ICE was the first described homologue of CED-3 and it is known that overexpression of ICE of CED-3 in Rat-1 fibroblasts induced apoptosis (8). Further studies also suggest that proteases of the ICE family may play an important role in the apoptotic mechanism.

ICE seems to be a pIL-1β specific processing enzyme, because it does not cleave IL-1α or several other proteins containing many Asp-X bonds.

Interleukin IL-1α and IL-1β are pleiotropic cytokines, which, although their sequences show scarce analogy, exert a variety of similar effects on different tissues and act on many human pathologies, in particular on the immunitary response of the organism and on inflammatory processes (9). Both proteins have a molecular weight of about 17.5 KDa and are previously synthesised as precursor molecules of larger size having a molecular weight of about 31 KDa.

IL-1s are potent inflammatory and pyrogenic cytokines that normally have beneficial effects but can also have extremely unhealthy effects for the organism. They can, for example, participate in the pathogenesis of symptoms of the autoimmune pathologies like systemic lupus erithematosus and, in particular, they are involved as mediators to provoke damages to tissues as for example in rheumatoid arthritis.

Many of the biological effects of IL-1 are similar to those that can be observed during a septic event. Recent studies demonstrated that the intravenous administration of IL-1 in doses from 1 to 10 ng/kg gives rise to fever, sleepiness, anorexia, generalised myalgia, arthralgia and cephalea.

Since IL-1s have pleiotropic biological activities, many of which influence negatively the organism, the powerful effects of IL-1 should be under strict physiological control.

IL-1 synthesis is inhibited by anti-inflammatory cytokines, prostaglandins and glucocorticoids and the existence of multiple levels of inhibition of IL-1 points to the necessity of a strict control of this mediator.

There are two types of IL-1 receptors named IL-1RI and IL-1RII. IL-1RII is a non-signalling IL-1 binding molecule which acts as a regulated decoy target for IL-1 (10–12).

An antagonist polypeptide for the receptor of IL-1 has been described up to now: the third known component until today of the family of the receptor-binding proteins is the antagonist for the IL-1 receptor (IL-1ra) (13–15). All three components (IL-1α, IL-1β, IL-1ra) recognise and bind to the same receptor on cell surface (IL-1R); IL-1α and IL-1β binding to IL-1R transmit a signal, whilst IL-1ra does not.

IL-1ra is a polypeptide which binds IL-1RI, and with less affinity IL-1RII, without any agonistic activity. IL-1ra production is induced in different cellular types, including mononuclear phagocytes, polymorphonuclear cells (PMN) and fibroblasts, by IgG. cytokines and bacterial products.

Until now two molecular forms of IL-1ra have been identified and cloned: 1) secreted IL-1ra (sIL-1ra) contains a classical leader sequence of 25 amino acids giving a mature protein of 152 amino acids; 2) intracellular IL-1ra (icIL-1ra) lacks a leader sequence thus allowing to predict that this protein remains intracellular.

sIL-1ra and icIL-1ra are generated from the same gene. icIL-1ra transcripts originate from an alternative starting site and from the splicing of a first alternative exon into an internal splice acceptor site located in the first exon of sIL-1ra. The predicted proteins are thus identical except in the NH$_2$ ends, where the first 21 amino acids of sIL-1ra are substituted by four amino acids in icIL-1ra.

Expression of transcripts encoding sIL-b 1ra and icIL-1ra is differently regulated. The biological significance of icIL-1ra is still unclear.

Considering that IL-1 is involved in pathogenesis of many diseases it is evident the need of having available medicaments useful to limit the unhealthy effects of IL-1.

A new molecular form of icIL-1ra has recently been identified and cloned (16 and PCT/EP95/04023). This molecule is generated by the in frame insertion of a new 63 bp exon between the first and the second exons of the icIL-1ra specific form. This new transcript has been found to be expressed in fibroblasts, keratimocytes, activated monocytes and polymorphonuclear cells. Expression in COS cells revealed that this new molecule is mostly intracellular and has a molecular weight of approximately 25 kDa in SDS-PAGE. Such new molecule has been called icIL-1ra type II (icIL-1raII). Considering that icIL-1raII is an intracellular protein as well as ICE, the Applicant has also tested the ability of icIL-1raII to inhibit ICE activity. The results are reported in the Examples of this patent application and show that icIL-1raII inhibits ICE activity.

DESCRIPTION OF THE INVENTION

The main object of the present invention is to provide new peptides capable of binding to ICE, thus blocking the production of the active form of IL-1β and/or, more generally, capable of binding to enzymes of the ICE family, thus blocking the activity of such enzymes. So the present invention relates to a peptide capable of binding to ICE and/or to enzymes of the ICE family, which peptide consists essentially of the amino acid sequence of SEQ ID NO:1, in which Xaa is selected between Asp and Ala, as specifically reported in SEQ ID NO:2 or 3. Optionally, the peptide also contains one or more amino acids at the N-terminal and/or the C-terminal end. Therefore, the peptide of the invention can be 19–40, preferably 19–25 amino acids long.

In particular, according to one embodiment of the invention, the peptide consists essentially of the amino sequence of SEQ ID NO:4 or 5.

A non-limiting list of cysteine proteases of the ICE family includes: CED-3 (17), Nedd-2/ICH-1 (18, 19), Yama/CPP-32/Apopain (20, 21, 22), Tx/ICH-2/ICE rel-II (23, 24, 25), ICE rel-III (25), Mch-2 (26), ICE-LAP3/Mch-3/CMH-1 (27, 28, 29), ICE-LAP-6 (30) and FLICE/MACH (31, 32).

Another object of the present invention is to provide the peptide in substantially purified form in order to be suitable for use in pharmaceutical compositions as active ingredient in pathologies that require ICE inhibition and/or inhibition of enzymes of the ICE family.

Examples of pathologies in which the new antagonist according to the invention can be advantageously used for prophylactic, therapeutic or diagnostic uses are lethal bacterial and viral infections as well as autoimmune and inflammatory diseases. Specific examples include: rheumatoid arthritis, septic shock, acute myelomonocytic leukaemia, immunological reaction of transplantation against host, acquired immunodeficiency syndrome (AIDS), ulcerative colitis and multiple sclerosis.

Further objects and advantages of the invention will be evident in the following description.

An embodiment of the invention is the administration of a pharmacological active amount of the peptide of the invention to subjects at risk of developing pathologies requiring ICE inhibition and/or inhibition of enzymes of ICE family or to subjects already showing such pathologies.

Any route of administration compatible with the active principle can be used, but particularly preferred is the parenteral administration because it permits to have, in short times, systemic effects. For this reason, it is preferable the administration of an intravenous bolus just before, during or after the surgical operation. The dose of peptide to be administered depends on the basis of the medical prescriptions according to age, weight and the individual response of the patient.

The dosage can be between 0.05 and 30 mg/Kg body weight and the preferable dose is between 0.1 and 10 mg/Kg body weight.

The pharmaceutical composition for parenteral use can be prepared in injectable form comprising the active principle and a suitable vehicle. Vehicles for the parenteral administration are well known in the art and comprise, for example, water, saline solution, Ringer solution and dextrose. The vehicle can contain smaller amounts of excipients in order to maintain the solution stability and isotonicity.

The preparation of the cited solutions can be carried out according to the ordinary modalities and preferably the peptide content will be comprised between 1 mg/ml and 10 mg/ml.

The present invention has been described with reference to the specific embodiments, but the content of the description comprises all modifications and substitutions which can be brought by a person skilled in the art without extending beyond the meaning and purpose of the claims.

The invention will now be described by means of the following Examples, which should not be construed as in any way limiting the present invention. The Examples will refer to the Figures specified here below.

DESCRIPTION OF THE FIGURES

FIG. 2: it shows a Western blotting analysis. pIL-1β was incubated with a monocytes lysate prepared as described in literature (4); after 60 minutes of incubation at 37° C. the mixture reaction was run on SDS-PAGE and the presence of precursor or mature IL-1β was evidenced by Western blotting. In particular, lane 1: pIL-1; and lane 2: pIL-1+monocytes lysate.

lane 2: pIL-1+peptide A;

lane 3: pIL-1+peptide B;

lane 4: pIL-1+peptide C;

lane 5: pIL-1+ICE;

lane 6: pIL-1+ICE+peptide A (2.5 µM);

lane 7: pIL-1+ICE+peptide A (0.25 µM);

lane 8: pIL-1+ICE+peptide B (2.5 µM);

lane 9: pIL-1+ICE+peptide B (0.25 µM);

lane 10: pIL-1+ICE+peptide C (2.5 µM); and lane 11: pIL-1+ICE+peptide C (0.25 µM).

lane 2: pIL-1+peptide B;

lane 3: pIL-1+peptide C;

lane 4: pIL-1+peptide X;

lane 5: pIL-1;

lane 6: pIL-1+ICE;

lane 7: pIL-1+ICE+peptide A (400 µM);

lane 8: pIL-1+ICE+peptide B (400 µM);

lane 9: pIL-1+ICE+peptide C (400 µM);

lane 10: pIL-1+ICE+peptide X (400 µM);

lane 11: pIL-1+ICE+peptide A (40 µM);

lane 12: pIL-1+ICE+peptide B (40 µM);

lane 13: pIL-1+ICE+peptide C (40 µM); and lane 14: pIL-1+ICE+peptide X (40 µM).

EXAMPLES

MATERIALS AND METHODS

Reagents

The following commercially available reagents were used for culture and separation of cells:

Ficoll (Seramed, Berlin. Germany), Percoll (Pharmacia, Uppsala, Sweden), RPMI 1640 (Seramed, Berlin, Germany), FCS (HycloneLaboratories, Logan, UK), Glutamine (Seramed, Berlin, Germany) and Hepes Merk, Darmastadt, Germany)

Cells

Mononuclear cells were obtained from the peripheral blood of human healthy donors by Ficoll gradient centrifugation. Purified monocytes were separated from mononuclear cells by Percoll gradient centrifugations at 2,000 rpm for 30 minutes at room temperature (10). COS-7 cells (purchased from ATCC, Rockville, Md., USA) and monocytes were cultivated in RPMI 1640 medium+10% FCS-2 mM glutamine+20 mM Hepes. Human recombinant IL-1β precursor was obtained from Cistron Biotechnology Pinebroom, N.J., USA. A polyclonal antibody reactive with both mature and precursors IL-1β was generated in this laboratory.

PCR

The ICE cDNA was obtained by RT-PCR, based on the published sequence (8a).

The RT-PCR was performed as described (16) for 30 cycles at 95° C. for 1 minute and 30 seconds, 55° C. for 1 minute and 30 seconds and 72° C. for 1 minute and 30 seconds. Oligonucleotides were obtained from Duotech (Milan, Italy). The sequences of oligos uses to selectively amplify ICE were as follows:

"FOR" ICE 1:5'-AAAAGCCATGGCCGACAAGGTC-3' (SEQ ID NO:9)
"REV" ICE 2:5'-TCTCTTCACCCTGCCCACAGAC-3' (SEQ ID NO:10).

RESULTS

Figure 3:
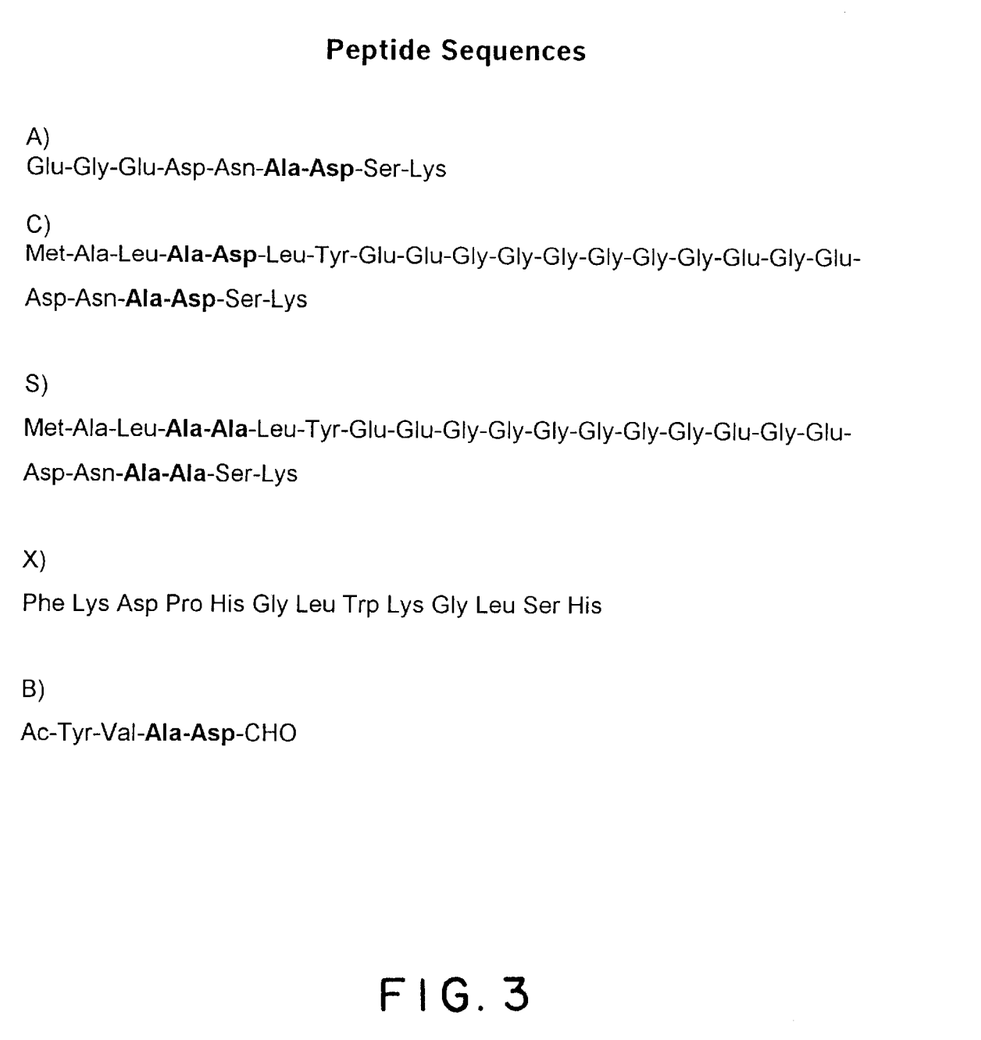
FIG. 3: it shows the amino acid sequences of the peptides under study. Peptide A (SEQ ID NO:6) and peptideC (SED ID NO:4) have been designed on the basis of icIL-1raII sequence. Peptide X (SEQ ID NO:7) is a randomly chosen peptide. Peptide S (SEQ ID NO:5) is identical to peptide C except for the presence of two Ala substituting the two Asp residues. Peptide B (SEQ ID NO:8) is a known ICE inhibitor (1a).
Figure 4:
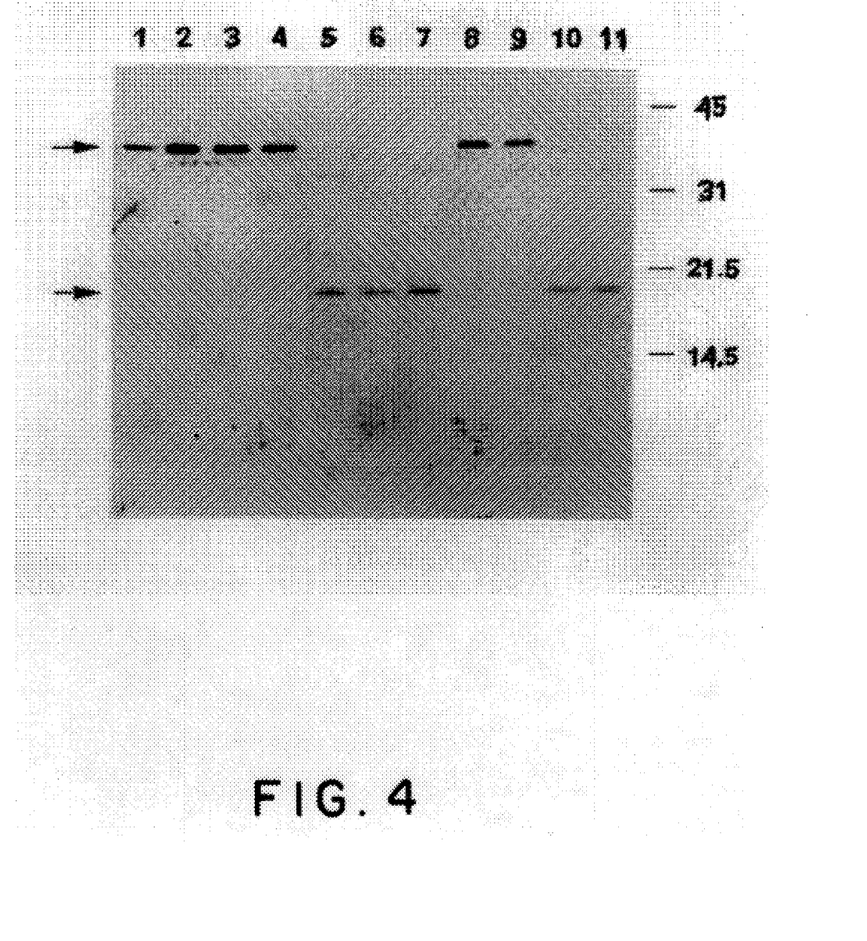
FIG. 4: it shows the inhibition of ICE activity by low concentrations of the peptides under study. pIL-1β (5 ng) was incubated with ICE in the presence or absence of peptides (0.25 or 2.5 µM) and the presence of precursor or mature IL-1β was evidenced as described for FIG. 2. In particular, lane 1: pIL-1.
Figure 5:
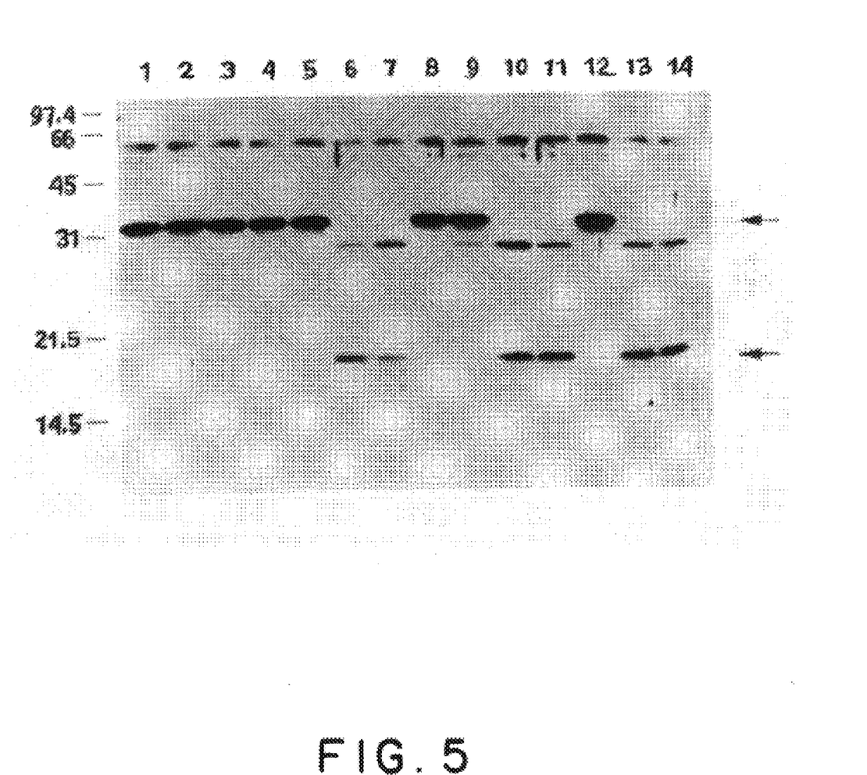
FIG 5: It shows the inhibition of ICE activity by high concentrations of the peptides under study. pIL-1β (5 ng) was incubated with ICE in the presence or absence of peptides (40 or 400 µM) and the presence of precursor or mature IL-1β was evidenced as described for FIG. 2. In particular, lane 1: pIL-1+peptide A.
Figure 6:
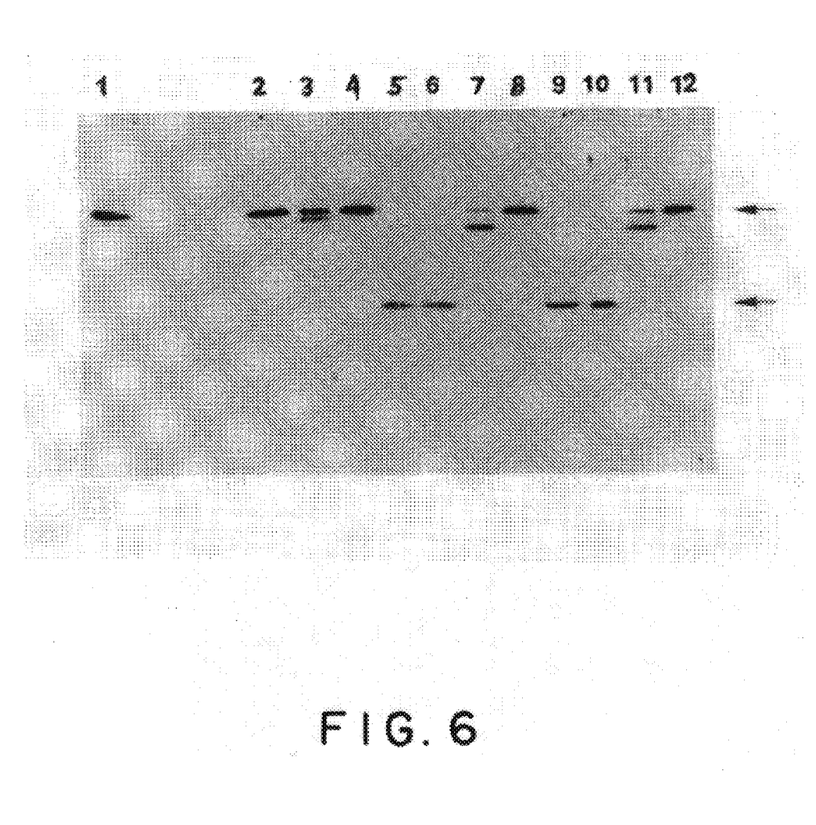
FIG. 6: It shows the inhibition of ICE activity by peptides C and S. pIL-1β (5 ng) was incubated with ICE in the presence or absence of peptides (100, 300 or 1,000 μM) and the presence of precursor or mature IL-1β was evidenced as described for FIG. 2. In particular, lane 1: pIL-1;
lane 2: pIL-1+peptide C;
lane 3: pIL-1+peptide S;
lane 4: pIL-1+peptide B;
lane 5: pIL-1+ICE,
lane 6: pIL-1+ICE+peptide C (0.1 mM);
lane 7: pIL-1+ICE+peptide C (0.3 mM);
lane 8: pIL-1+ICE+peptide C (1 mM);
lane 9: pIL-1+ICE+peptide S (0.1 mM);
lane 10: pIL-1+ICE+peptide S (0.3 mM);
lane 11: pIL-1+ICE+peptide S (1 mM); and
lane 12: pIL-1+ICE+peptide B (1 mM).

Expression of recombinant ICE enzyme in COS cells cDNA coding for human ICE has been amplified by PCR. The sequence was confirmed and the cDNA was subcloned into pSG5 expression vector. COS cells were transfected with empty vector (mock) or vector containing ICE cDNA and after 48 hours, cells were analysed for the expression of ICE specific mRNA. As shown in FIG. 3, COS cells, transfected with ICE cDNA, expressed high levels of ICE mRNA.

Figure 1:
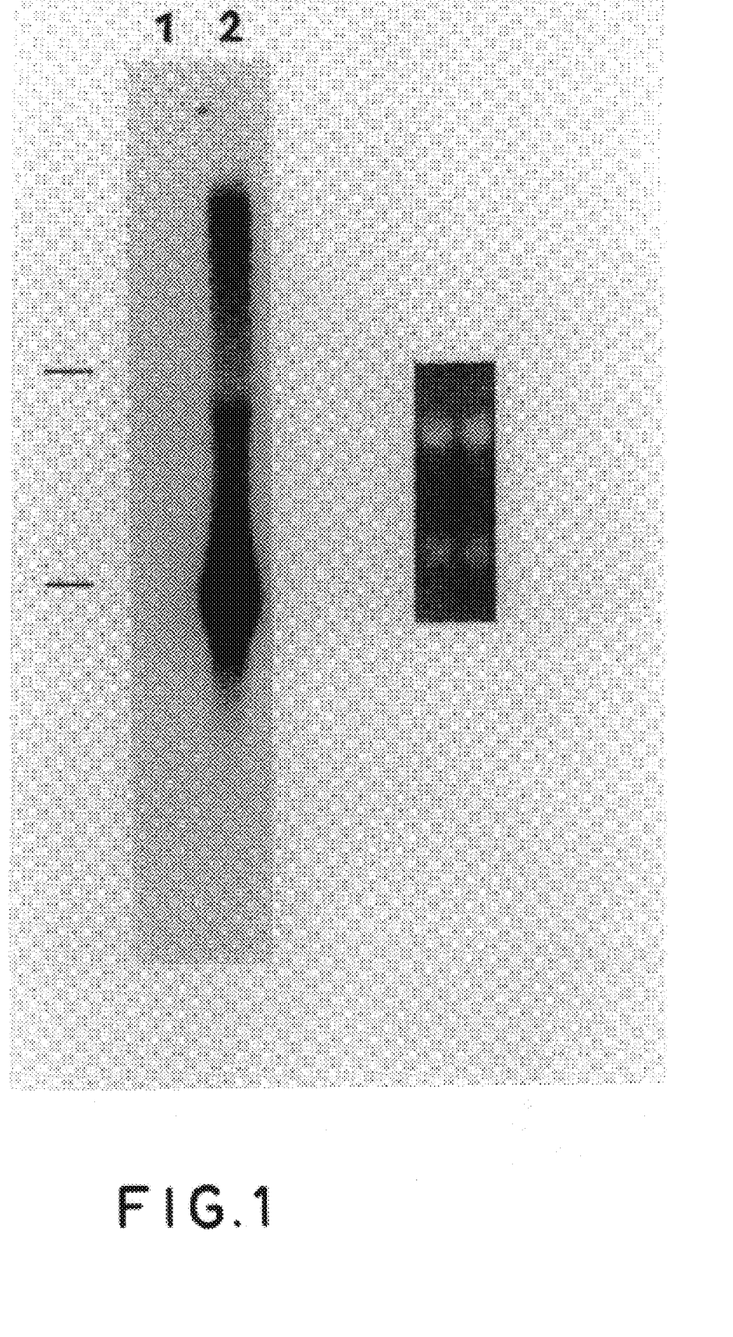
FIG. 1: it shows a Northern analysis of ICE mRNA expression in COS transfected cells. Total mRNA extracted by COS cells transfected with mock vector or with cDNA coding for human ICE was analysed by Northern analysis to evidence the expression of ICE specific mRNA. In particular, lane 1: MOCK; lane 2: ICE.
Figure 2:
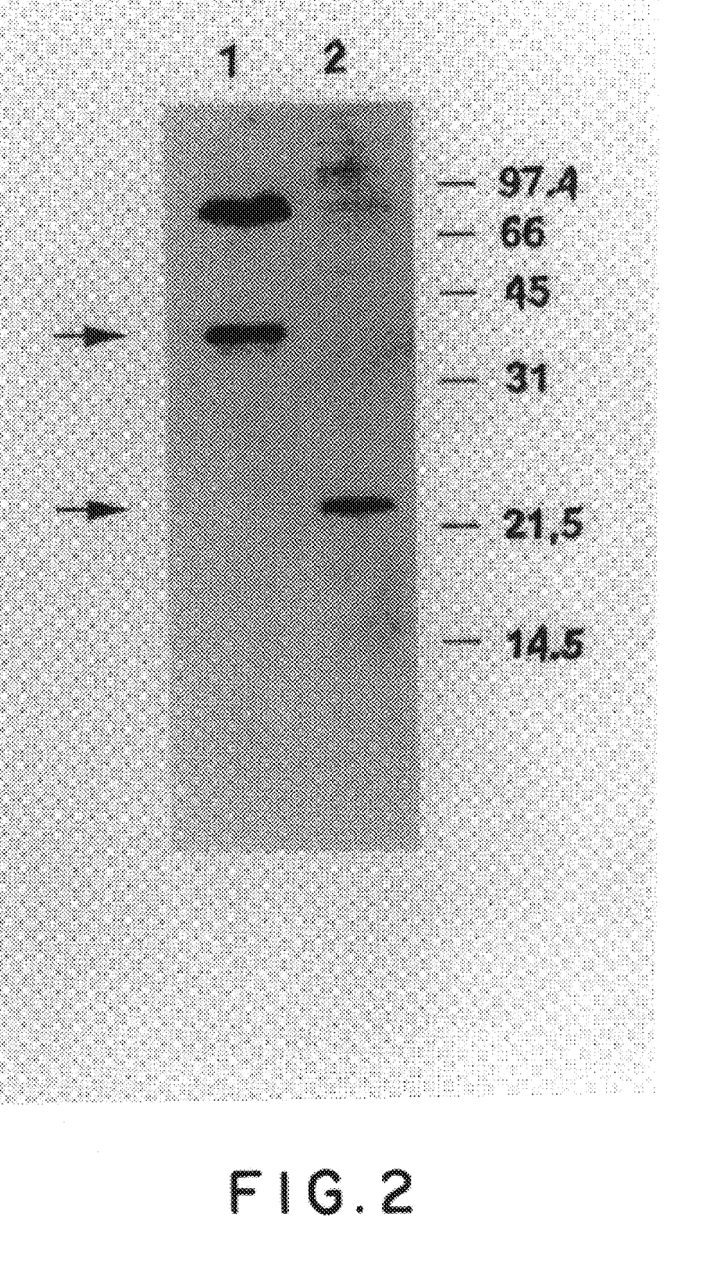

A monocyte lysate, prepared as previously described (11), was also able to convert pIL-1β into a mature form (FIG. 2). Therefore, recombinant ICE or freshly isolated human monocytes were used as a source of ICE enzymatic activity for further experiments.

Inhibition of ICE activity.

A source of ICE activity was prepared and its ability to cleave pIL-1β was tested by incubating the reaction at 37° C. for 1 hour. The mixture was then run on SDS-PAGE and the presence of pIL1-β or the mature form was evidenced by Western Blotting.

Four different peptides were designed, synthesised and tested for their ability to inhibit ICE activity. These peptides are indicated in FIG. 3 and were obtained by solid phase synthesiser from Applied Biosystems (Foster City, Calif.). Purity of these peptides was verified by high pressure liquid chromatography.

The tetrapeptide B (Bachem, Bubendorf, Switzerland) reported in FIG. 3, which is a known ICE inhibitor (1a), was used as positive control.

References 1. a) Thornberry et al., A novel cysteine protease is required for interleukin-1β processing in monocytes, Nature, 356, 768–774, 1990; b) Ceretti et la., Molecular cloning of the interleukin-1β converting enzyme, Science, 256, 97–100, 1992;

2. Cameron et al., Amino acid sequence analysis of human IL-1. Evidence for biochemically distinct forms of IL-1, J. Exp. Med., 162, 790–801, 1985;

3. Mosley et al., The interleukin-1 receptor binds the human interleukin-1α precursor but not the interleukin-1β precursor, J. Biol. Chem., 262, 2941–2944, 1987;

4. Kostura et al., Identification of a monocyte specific pre-interleukin-1β convertase activity, Proc. Natl. Acad. Sci. USA, 86, 5227–5231, 1989;

5. Black et al., Activation of interleukin-1β by a co-induced protease, FEBS Lett., 427, 386–390, 1989;

6. Howard et al., IL-1 converting enzyme requires aspartic acid for processing of the IL-1β precursor at two distinct sites and does not cleave 31 kDa IL-1α, J. Immunol., 147, 2964–2969, 1991;

7. Griffin et al., III Int. J. Mass. Spectrom. Ion. Phys., 11, 131–149, 1991;

8. Miura et al., Induction of apoptosis in fibroblasts by interleukin-1β-converting enzyme, a mammalian homologue of the C. elegans cell death gene ced-3, Cell, 75, 653–660, 1993.

9. Dinarello, Interleukin-1 and interleukin-1 antagonism, Blood, 77, 1627–1652, 1991;

10. Colotta et al., Interleukin-1 type II receptor: a decoy target for IL-1 that is regulated by IL-4, Science, 261, 472–475, 1993;

11. Sims et al., Interleukin-1 signalling occurs exclusively via the type I receptor, Proc. Natl. Acad. USA, 90, 6155–6159, 1993;

12. Colotta et al., Immunol. Today, 15, 562–566, 1994;

13. Hannum et al., Interleukin-1 receptor antagonist activity of a human interleukin-1 inhibitor, Nature, 343, 336–340, 1990;

14. Eisenberg et al., Primary structure and functional expression form complementary DNA of a human interleukin-1 receptor antagonist, Nature, 343, 341–346, 1990;

15. Carter et al., Purification, cloning, expression and biological characterisation of an interleukin-1 receptor antagonist protein, Nature, 344, 633–638, 1990;

16. Muzio et al., Cloning and characterisation of a new isoform of interleukin-1 (IL-1) receptor antagonist (IL1ra), J. Exp. Med., 182623, 1995;

17. Yuan et al., The C. elegans cell death gene ced-3 encodes a protein similar to mammalian interleukin-1β-converting enzyme, *Cell*, 75, 641–652, 1993;

18. Kumar et al., Induction of apoptosis by the mouse nedd2 gene, which encodes a protein similar to the product of the C. elegans cell death gene ced-3 and the mammalian interleukin-1β-converting enzyme, *Genes Dev.* 8, 1613–1626, 1994;

19. Wang et al., Ich-1, an Ice/ced-3-related gene, encodes both positive and negative regulators of programmed cell death, *Cell*, 78, 739–750, 1994;

20. Fernandes-Alnemri et al., CPP-32, a novel human apoptotic protein with homology to *Caenorhabditis elegans* cell death protein CDE-3 and mammalian interleukin-1β-converting enzyme, *J. Biol. Chem.*, 269, 30761–340764, 1994;

21. Nicholson et al, Identification and inhibition of ICE/CED-3 protease necessary for mammalian apoptosis, *Nature*, 376, 37–43, 1995;

22. Tewari et al., Yama/CPP-32β, a mammalian homologue of CED-3, is a CmA-inhibitable protease that cleaves the death substrate poly(ADP-ribose) polymerase, *Cell*, 81, 801–809, 1995;

23. Faucheu et al., A novel human protease similar to the interleukin-1β-converting enzyme induces apoptosis in transfected cells, *EMBO J.*, 14, 1914–1922, 1995;

24. Kamens et al., Identification and characterisation of ICH-2, a novel member of the interleukin-1β-converting enzyme family of cysteine proteases, *J. Biol. Chem.*, 270, 15250–15256, 1995;

25. Munday et al., Molecular cloning and proapoptotic activity of ICE rel-II and ICE rel-III, members of the ICE/CED-3 family of cysteine proteases, *J. Biol. Chem.*, 270, 15870–15876, 1995;

26. Fernandes-Alnemri et al., Mch-2, a new member of the apoptotic CED-3/ICE cysteine protease gene family, *Cancer Res.*, 55, 2737–2742, 1995;

27. Duan et al., ICE-LAP3, a novel mammalian homologue of the *Caenorhabditis elegans* cell death protein CED-3, is activated during Fas- and TNF-induced apoptosis, *J. Biol. Chem.*, 2271, 35013–35035, 1996;

28. Fernandes-Alnemri et al., Mch-3, a novel human apoptotic cysteine protease highly related to CPP-32, *Cancer Res.*, 55, 6045–6052, 1995;

29. Lippke etal., Identification and characterisation of CPP-32/Mch-2 homologue 1, a novel cysteine protease similar to CPP-32, *J. Biol. Chem.*, 271, 1825–1828, 1996;

30. Duan et al., ICE-LAP6, a novel member of the ICE/Ced-3 gene family, is activated by the cytotoxic T cell protease granzyme B, *J. Biol. Chem.*, in press 1996

31. Muzio et al., FLICE a novel FADD-homologous ICE/CED-3-like protease, is recruited to the CD95(FAS/Apo-1) Death-Inducing Signalling Complex, Cell, 85, 817–827, 1996;

32. Boldin et al., Involvement of MACH, a novel MORT-1/FADD-interacting protease, IN Fas/Apo-1- and TNF receptor-induced cell death, *Cell*, 85, 803–815, 1996.

What is claimed is:

1. A peptide which consists of the amino acid sequence of SEQ ID NO:1, in which Xaa is selected between Asp and Ala.

2. The peptide according to claim 1, consisting of the amino acid sequence of SEQ ID NO:2.

3. The peptide according to claim 1, consisting of the amino acid sequence of SEQ ID NO:3.

4. A peptide consisting of 20–40 amino acid residues in which one or more amino acid residues are added to the N-terminal and/or C-terminal end of SEQ ID NO:1 and wherein at least one of two Xaa residues of SEQ ID NO:1 is Ala.

5. The peptide according to claim 4, consisting of the amino acid sequence of SEQ ID NO:4.

6. The peptide according to claim 4, consisting of the amino acid sequence of SEQ ID NO:5.

7. The peptide of claim 4, wherein both Xaa residues of SEQ ID NO:1 are Ala.

8. Pharmaceutical compositions containing the peptide according to claim 1 together with one or more pharmaceutically acceptable carriers and/or excipients.

9. Pharmaceutical compositions according to claim 8, wherein the pathology is selected from the group of autoimmune diseases.

10. Pharmaceutical compositions according to claim 8, wherein the pathology is selected from the group consisting of lethal bacterial and viral infections.

11. Pharmaceutical compositions according to claim 8, wherein the pathology is selected from the group consisting of inflammatory diseases.

12. A method for inhibiting ICE and/or an enzyme of the ICE family, comprising administering the peptide according to claim 1 to a subject in need thereof.

13. The method according to claim 12, wherein the subject in need thereof suffers from an autoimmune disease.

14. The method according to claim 12, wherein the subject in need thereof suffers from an inflammatory disease.

15. The method according to claim 12, wherein the subject in need thereof suffers from bacterial and viral infections which can be lethal.

16. A pharmaceutical composition containing the peptide according to claim 4 together with one or more pharmaceutically acceptable carriers and/or excipients.

17. A method for inhibiting ICE and/or an enzyme of the ICE family, comprising administering the peptide according to claim 4 to a subject in need thereof.

18. The method according to claim 17, wherein the subject in need thereof suffers from an autoimmune disease.

19. The method according to claim 17, wherein the subject in need thereof suffers from an inflammatory disease.

20. The method according to claim 17, wherein the subject in need thereof suffers from bacterial and viral infections which can be lethal.

* * * * *